US 6,603,556 B2

(12) United States Patent
Belz et al.

(10) Patent No.: US 6,603,556 B2
(45) Date of Patent: Aug. 5, 2003

(54) PHOTOMETRIC DETECTION SYSTEM HAVING MULTIPLE PATH LENGTH FLOW CELL

(75) Inventors: Mathias Belz, Sarasota, FL (US); Su Yi Liu, Sarasota, FL (US); Richard L. Miller, Flidell, LA (US)

(73) Assignee: World Precision Instruments, Inc., Sarasota, FL (US)

( * ) Notice: Subject to any disclaimer, the term of this patent is extended or adjusted under 35 U.S.C. 154(b) by 0 days.

(21) Appl. No.: 09/975,164

(22) Filed: Oct. 11, 2001

(65) Prior Publication Data

US 2002/0071123 A1 Jun. 13, 2002

Related U.S. Application Data

(60) Provisional application No. 60/239,742, filed on Oct. 12, 2000.

(51) Int. Cl.⁷ .............................................. G01N 21/00
(52) U.S. Cl. ...................... 356/440; 356/436; 356/246; 385/125
(58) Field of Search ................... 356/244, 246, 356/432, 436, 440; 385/12, 13, 125; 250/227.25, 227.19, 576, 227.11

(56) References Cited

U.S. PATENT DOCUMENTS

| | | | | |
|---|---|---|---|---|
| 5,168,367 A | * | 12/1992 | O'Rourke et al. | 356/246 |
| 5,184,192 A | | 2/1993 | Gilby et al. | 356/246 |
| 5,268,736 A | * | 12/1993 | Prather | 356/246 |
| 5,302,272 A | * | 4/1994 | Klein | 356/344 |
| 5,416,879 A | | 5/1995 | Liu | 385/125 |
| 5,442,437 A | * | 8/1995 | Davidson | 356/246 |
| 5,444,807 A | | 8/1995 | Liu | 385/125 |
| 5,452,082 A | * | 9/1995 | Sanger et al. | 356/246 |
| 5,570,447 A | | 10/1996 | Liu | 385/125 |
| 5,593,564 A | * | 1/1997 | Templin et al. | 204/451 |
| 5,604,587 A | | 2/1997 | Che et al. | 356/246 |
| 5,608,517 A | | 3/1997 | Munk | 356/246 |
| 5,876,674 A | * | 3/1999 | Dosoretz et al. | 422/91 |
| 6,016,372 A | | 1/2000 | Fein et al. | 385/12 |

OTHER PUBLICATIONS

"Measuring The Absorption of CDOM In The Field Using A Multiple Pathlength Liquid Waveguide System" by Richard L. Miller, Mathias Belz, and Su Yi Liu, Published in Ocean Optics XV, 2000, Paper 001308, pp. 1–8.

"Linearity and Effective Optical Pathlength of Liquid Waveguide Capillary Cells" by Mathias Belz, Peter Dress, Aleksandr Sukhitskiy and Suyi Liu, SPIE vol. 3856, pp. 271–281.

\* cited by examiner

*Primary Examiner*—Hoa Q. Pham
(74) *Attorney, Agent, or Firm*—Alix, Yale & Ristas, LLP

(57) ABSTRACT

A photometric detection system including a light source, a photometric detector, and a flow cell assembly. The flow cell assembly includes a tubular liquid core waveguide having inlet and discharge ends for receiving and discharging a flow of the sample fluid. A first coupling device optically couples the light source to the waveguide at a first position along the length of the waveguide. A second coupling device optically couples the detector to the waveguide at a second position along the length of the waveguide. The first and second positions define an optical path length within the waveguide. The second position is variable relative to the first position such that the optical path length is selectively varied.

9 Claims, 4 Drawing Sheets

PHOTOMETRIC DETECTION SYSTEM HAVING MULTIPLE PATH LENGTH FLOW CELL

CROSS-REFERENCE TO RELATED APPLICATIONS

This application claims the benefit under 35 U.S.C. §119 (e) of U.S. Provisional Patent Application Serial No. 60/239,742 filed Oct. 12, 2000.

The U.S. Government has a paid-up license in this invention and the right in limited circumstances to require the patent owner to license others on reasonable terms as provided for by the terms of Contract Nos. NCC13-9903 and NCC13-9903-Supplement No. 2 awarded by the National Aeronautics and Space Administration.

BACKGROUND OF THE INVENTION

This invention relates generally to photometric apparatus for spectroscopic analysis of samples in solution. More particularly, the present invention relates to photometric apparatus having a flow cell for aqueous solutions.

A range of optical flow cells have been developed for absorption spectroscopy applications in the ultraviolet, visible and infrared regions of the light spectrum. As defined by the Beer-Lambert's Law, absorbance (A) of light by a sample is proportional to the chromophore concentration (c), the molar absorption coefficient ($\epsilon$), and the optical path length (1)

$$A = \epsilon l c = log(I/I_0) \text{ (Beer's Law)}$$

where I is the transmitted light power through the cell with sample solution and $I_0$ is the light power transmitted trough the sample with a reference solution. In oceanography, the absorbtion of light (a) is defined as a=2.303A, where A is the absorbance of light and the optical path length (1) is specified to be 1 meter.

There are two ways by which the sensitivity of an optical sensor cell can be increased. First, the intrinsic noise of the spectrophotometer used could be reduced. For example most spectrophotometers exhibit typical noise levels equivalent to milli absorbance units (mAU). However, noise levels in spectrophotometers used in liquid chromatography are typically 100 (AU or less. The second approach is to increase the optical path length of the sample cell. However, using conventional technology, it is difficult to transmit a collimated light beam for extended distances in fluids without either very substantial light loss or, the use of advanced and very expensive collimating optics. This problem is exacerbated when the diameter of the cell must be as small as possible, in general, a requirement for most flow-through detector applications.

To overcome this problem, a light guiding flow cell is formed when an analyte solution functions as the core of a fluid filled light waveguide. Similar to optical fibers, light is confined within the (liquid) core by total internal reflection at the core/wall interface. Such flow cells are particularly suitable when combined with optical fibers for light transfer, enabling the design of a flexible sensor system. A number of flow cells with long optical path lengths have been designed for absorbance, fluorescence and Raman spectroscopy.

Such flow cells can be divided into two types on the basis of the light guiding effect and practical observations. Type I flow cells rely on the principle that the core fluid is in direct contact with the wall material (cladding) having a lower refractive index than the core fluid (U.S. Pat. Nos. 5,184, 192, 5,416,879, 5,444,807, 5,604,587, and 5,608,517). Typical wall materials used for aqueous solutions include a copolymer of 2,2 bis trifluoromethyl-4,5 difluoro-1,3 dioxole with tetrafluoroethylene (Dupont "Teflon AF"). Teflon AF has a refractive index between 1.29 and 1.31, is chemically very inert and transparent within the 200 nm to 2000 nm spectral range. Because Teflon AF could be used to coat the internal surface of e.g. glass tubing and later could be drawn directly to tubing, it created a number of useful opportunities in the development of flow cells with long optical path lengths.

In Type II flow cells, the low refractive cladding material is not in direct contact with the core fluid, but separated by a transparent high-refractive index wall which does not interfere with the waveguide properties of the cell. The early development of waveguide sample cell technology was made difficult by the absence of a suitable cladding material which possessed a refractive index lower than that of water (n=1.33), a most commonly used solvent. This problem was originally solved by using a bar quartz capillary suspended in air. In this arrangement, light would be reflected at the outer air/glass interface. However, light transmission was found to be strongly dependent on the cleanliness of the external cell surface. Ambient dust and fingerprint contamination could easily degrade light transmission and thus the reproducibility of the analytical measurements. Tiny cracks could develop at the external surface resulting in a brittle, easily broken capillary cell. With the availability of TEFLON AF, the outside surface of a glass or fused silica capillary cell could be coated with Teflon AF producing a similar effect. The advantage of this configuration was that the total reflection would occur at the fused silica wall/Teflon AF interface and cell surface contamination could not alter the waveguide properties of Type II cells. Moreover, the fused silica tubing used in the Type II Liquid Waveguide Capillary Cell (LWCC) acted like a backbone, providing physical stability to the cell with the Teflon AF coating protecting its external surface from mechanical crack formation. The tubing could be made with a very thin wall and spooled if required (U.S. Pat. Nos. 5,416,879, 5,444,807, and 5,604,587). The hydrophilic surface of the inner silica surface reduced internal air bubble formation, which is a major problem of small diameter Type I cells, where the hydrophobic Teflon AF tends to trap air bubbles at the inner cell wall.

There are two major draw backs with the current flow cell technology and usage of single path length flow cells in general. First, all flow cells currently built are designed for low volume applications, such as liquid chromatography (LC), high pressure liquid chromatography (HPLC), or fluid injection analysis (FIA). Particles and air bubbles are easily trapped in such cells, making them difficult to use for routine sensitive laboratory or process type analysis. Further, following Beers law, the concentration of a sample is proportional to absorbance of the chromophore, which is the logarithm of the incident, $I_0$, and transmitted light, (I) through the sample. Although the sensitivity of the measurement can be increased by increasing the optical path length, l, of the flow, cell, still the fact that the concentration—intensity relationship is logarithmic, severely limits the dynamic range of a measurement. This contrasts to for example fluorescence measurements, where the relationship of sample concentration and emission intensity is linear, thus exhibiting a far higher dynamic range.

Ideally, the optical path length of a sample cell for absorbance-based flow cell should be changeable to allow for a higher dynamic range. A typical area, where a larger dynamic range than available from a single sample cell is required is found in the field of oceanography. Routinely, the concentration of colored dissolved organic matter (CDOM), which is a significant component of the bulk absorption of light in coastal waters, is determined.

The spectral absorption of CDOM is frequently an important element of bio-optical models and remote sensing algorithms for near shore waters. Traditional methods of measuring the absorption of dissolved materials require special handling and storage prior to measurement using expensive laboratory spectrophotometers. Thus, the availability of CDOM absorption measurements are often scarce or totally lacking, particularly in the optically complex and CDOM rich environment of river-dominated coastal margins. This lack of CDOM measurements limits the ability to derive appropriate regional-to-global scale mathematical color models for chlorophyll pigments and primary productivity in fresh and sea water. CDOM concentrations vary significantly between open ocean samples (0.007 $m^{-1}$ at 380 nm) and high turbidity freshwater environments with absorption as high as 10–20 $m^{-1}$ at 380 nm. This requires a higher dynamic range than a detection system based on a single path length flow cell can provide.

SUMMARY OF THE INVENTION

Briefly stated, the invention in a preferred form is a photometric detection system which comprises a light source, a photometric detector, and a flow cell assembly. The flow cell assembly includes a tubular liquid core waveguide having inlet and discharge ends for receiving and discharging a flow of the sample fluid. A first coupling device optically couples the light source to the waveguide at a first position along the length of the waveguide. A second coupling device optically couples the detector to the waveguide at a second position along the length of the waveguide. The first and second positions define an optical path length within the waveguide. The second position is variable relative to the first position such that the optical path length is selectively varied.

The second coupling device may comprise a plurality of collector optical fibers with the light receiving end of each collector optical fiber coupled to the waveguide at a collection position longitudinally spaced from the collection position of each other collector optical fiber. Each of the light emitting ends of the collector optical fibers is optically coupled to an input port of an optical switch. An outlet port of the optical switch is optically coupled to the photometric detector. The optical switch provides for selectively coupling any one of the optical path lengths to the detector. In one alternative, the first coupling device comprises a plurality of emitter optical fibers with the light emitting end of each collector optical fiber coupled to the waveguide at an emission position longitudinally spaced from the emission position of each other collector optical fiber. Each of the light receiving ends of the emitter optical fibers is optically coupled to an output port of an optical switch. An input port of the optical switch is optically coupled to the light source. In a second alternative, the first coupling device and the second coupling device both comprise a plurality of optical fibers having one end coupled to an optical switch.

In one embodiment of the flow cell assembly, first, second, third and fourth collector optical fibers are coupled to the waveguide at collection positions longitudinally spaced 2 cm, 10 cm, 50 cm and 200 cm, respectively, from the first position. Preferably, the length of the waveguide is 200 cm and the collection position for the fourth collector optical fiber is proximate to the discharge end of the waveguide. In a second embodiment of the flow cell assembly, first, second and third collector optical fibers are coupled to the waveguide with the collection position for the third collector optical fiber being proximate to the discharge end of the waveguide.

In a third embodiment of the flow cell assembly, the second coupling device comprises a single collector optical fiber. The light receiving end of the collector optical fiber is longitudinally moveable within the waveguide. A drive mechanism engaged with the collector optical fiber provides a means of moving the collector optical fiber within the waveguide. The collector optical fiber includes a hermetically sealed buffer coating. A polyimide coating may be disposed on the buffer coating. Alternatively, the light emitting end of the emitting optical fiber may be moveable within the waveguide or both the emitting optical fiber and the collector optical fiber may be moveable within the waveguide.

It is an object of the invention to provide a photometric detection system having a greater dynamic range than is available from conventional systems.

It is also an object of the invention to provide a flow cell assembly for a photometric detection system having multiple optical path lengths.

Other objects and advantages of the invention will become apparent from the drawings and specification.

BRIEF DESCRIPTION OF THE DRAWINGS

The present invention may be better understood and its numerous objects and advantages will become apparent to those skilled in the art by reference to the accompanying drawings in which.

DETAILED DESCRIPTION OF THE PREFERRED EMBODIMENT

Conventional photometric detection systems employ a single sample cell which generally has a noise level of approximately 0.001 AU at zero absorbance and can be used within its linear range to measure absorbencies as high as 2 absorbance units (AU). In certain applications however, a larger dynamic range is required than can be provided by such a single cell arrangement. For example, certain oceanographic applications require the measurement of the absorption of colored dissolved organic matter (CDOM). The absorbtion spectra required to measure the CDOM may be in the range of 0.007 $m^{-1}$ to 30 $m^{-1}$, requiring an approximate four thousand fold dynamic range for the detector system. A photometric detection system in accordance with the invention includes a sample cell assembly having multiple optical path lengths which together provide the required dynamic range.

Figure 1:
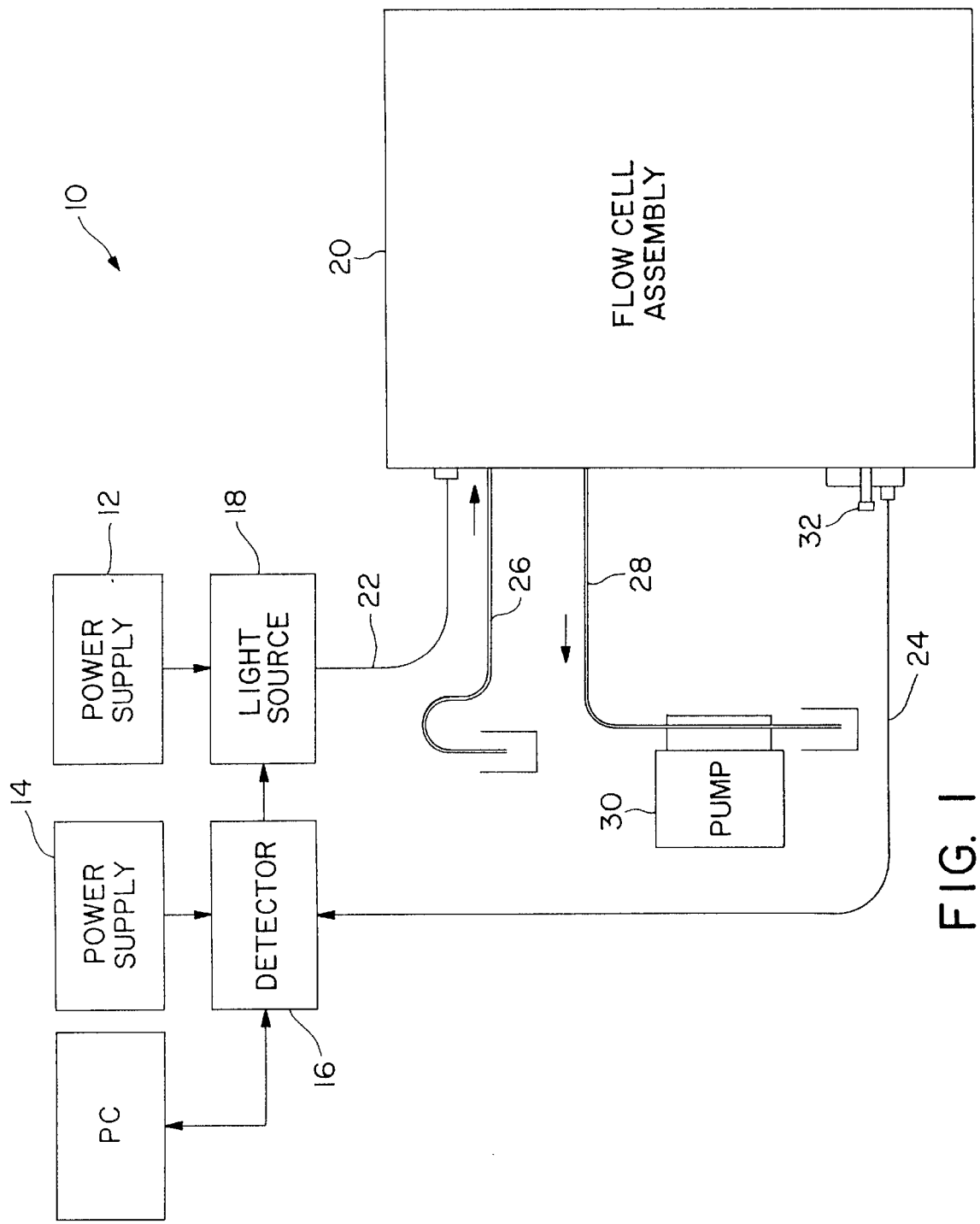
FIG. 1 is a schematic diagram of a photometric detection system in accordance with the invention.

With reference to FIG. 1, a photometric detection system 10 in accordance with the invention includes one or more power supplies 12, 14 for providing power to a detector module 16 (for example a spectrometer) and a light source 18. The detector module 16 may be connected to a computer (PC). Light emitted from the light source 18 is coupled into the liquid core waveguide or flow cell 36, 70, 96 of the flow cell assembly 20 with an input optical fiber 22. Light is collected from the flow cell assembly 20 with an output optical fiber 24 and guided to the detector module 16. The liquid sample is transferred into and out of the flow cell assembly 20 via sample inlet and sample discharge tubes 26, 28. The diameter of the fluid path is kept as uniform as possible to avoid pressure differences which could result in the generation of micro air bubbles. A pump 30 connected to the sample discharge tube 28 is used to draw the sample through the flow cell assembly 20. A path length selection device 32 (optical switch) is used to selectively couple the light from a particular path length to the detector module 16. Thus the absorbance of a sample solution (e.g. water) can be determined within the wavelength region of interest.

The flow cell design, exemplified here, is based on a Type I liquid core waveguide, preferably made of Dupont Teflon AF™ tubing, however, a Type II waveguide may be substituted with little difficulty. The optical throughput of small diameter (e.g., ID<600 $\mu$m) liquid waveguides is highly sensitive to contamination on the waveguide internal surface. Surface contamination and the trapping of air bubbles are minimized in the subject flow cell 36, 70, 96 by employing a large core tube, having an inner diameter in the range of 0.1–100 mm, preferably in the range of 1–10 mm, and a wall thickness of 0.005 to 10 mm. Larger dimensions may be possible, for example in process analysis cells. The larger core diameter of the waveguide results in a decrease of the number of reflections at the water core-waveguide interface. Furthermore, due to the smaller internal curvature of the large core tube, less air bubbles are trapped inside the cell 36, 70, 96 and can be removed more easily. Scattering caused by small particles, either flowing inside the cell 36, 70, 96 or adhering to the cell wall, is also reduced.

The subject photometric detection system 10 provides measurements in the region of 0.001 to approximately 2 AU. However, sufficiently detailed absorbance spectra can be expected in the range of 0.05 AU to 1.0 AU (which corresponds to 10% and 90% attenuation respectively), resulting in a twenty-fold dynamic range (1.0/0.05=20) of the detection system. To increase the sensitivity of a detection system 10, the optical path length of the flow cell 36, 70, 96 can be increased. To increase the dynamic range of such a detection system, flow cells of different optical path length can be used in such a way that the lower detection limit of each shorter length cell matches the higher measurement limit of the next longer length cell.

In a first embodiment of the sample cell assembly 34 (FIG. 2), the light in an elongated flow cell 36, or waveguide, is selectively captured at a number of predetermined positions 38, 40, 42, 44 along the length of the flow cell 36 to thereby provide multiple optical paths 46, 48, 50, 52 within a single flow cell 36. An optical coupler 54 couples the light out of the flow cell 36 at each of the positions 38, 40, 42, 44 via the cell wall. The flow cell 36 may include multiple flow cell sections, each defining an inlet and an outlet, with one or more of the positions 38, 40, 42, 44, being disposed in each of the sections.

Alternatively, a single collector optical fiber optically coupled at one end of the flow cell 36 and a plurality of emitter optical fibers optically coupled to the flow cell 36 at longitudinally spaced positions will also provide multiple optical paths. In addition, multiple collector optical fibers, which are optically coupled to the flow cell 36 at longitudinally spaced positions, and multiple emitter optical fibers, which are optically coupled to the flow cell 36 at longitudinally spaced positions will also provide multiple optical paths.

Five possible coupling methods are possible with Type I and Type II waveguides. In a first method, the flow cell wall is polished to a D-shape and light is coupled into the waveguide with an optical fiber. The optical fiber preferably has an angular polished fiber tip to increase coupling efficiency. In a second method, the optical fiber and the flow cell are fused together utilizing the fused bionic taper (FBT) method. In a third method, prism coupling is used to couple light out off the flow cell. In a fourth method, the flow cell is composed of solid Teflon™, allowing the coupling optical fiber to be directly fixed into the flow cell wall. In the fifth method, a hole is drilled into the waveguide wall and the optical fiber is inserted into the waveguide core. All these coupling techniques are optimized to ensure that the obstruction of the light path does not result in a loss greater than 30–40% of the total light power coupled into the flow cell per coupling.

Figure 2:
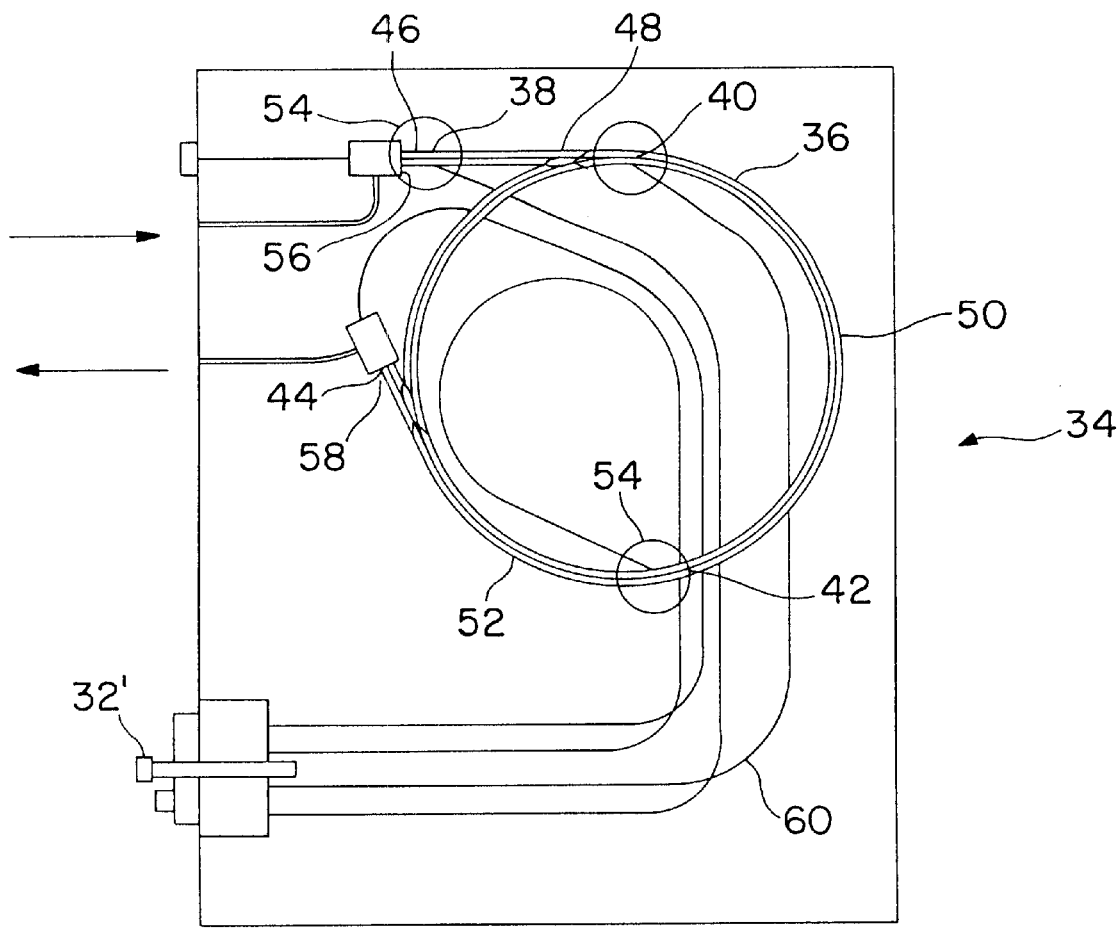
FIG. 2 is a schematic diagram of a first embodiment of the flow cell assembly of FIG. 1.

In the embodiment of FIG. 2, four optical path lengths are selected to cover the requested dynamic range, 2 cm, 10 cm, 50 cm and 200 cm. It should be appreciated that the path length increases about 4 to 6 times with each successive optical path 46, 48, 50, 52. The dynamic range of this optimized system will be at least a 10 fold up to 100 fold improvement, when using a measurement range of 0.1 to 1 AU and 0.001 to 2 AU respectively, compared to a conventional single absorbance cell.

The flow cell 36 has inlet and discharge ends 56, 58 coupled to the inlet and discharge tubes 26, 28, respectively, and preferably has a length of 200 cm, allowing the 200 cm position optical coupler 54 to be positioned at the discharge end 58 of the flow cell 36. The flow cell 36 is coiled to reduce the overall footprint of the flow cell assembly 34. The input optical fiber 22 is coupled to the inlet end 56 of the flow cell 36. The 2 cm, 10 cm, 50 cm and 200 cm position optical couplers 54 are each coupled to the proximal end of a collector optical fiber 60. An optical switch 32' with four positions is coupled to the distal ends of the collector optical fibers 60 and is used to selectively couple the light from a particular path length to the detector module 16.

Figure 3:
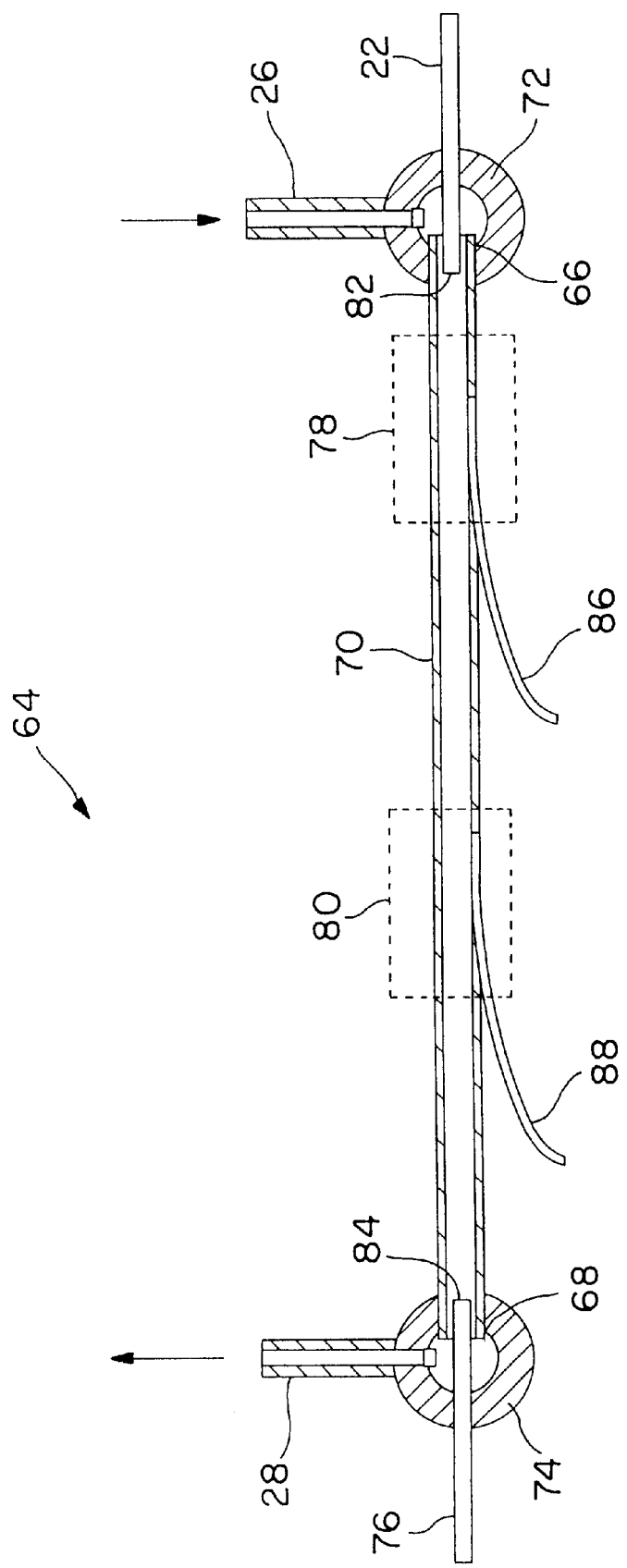
FIG. 3 is a schematic diagram of a second embodiment of the flow cell assembly of FIG. 1.

In a second embodiment of the flow cell assembly 64 (FIG. 3), the inlet and discharge ends 66, 68 of the flow cell 70 are mounted to the inlet and discharge tubes 26, 28 by inlet and outlet couplings 72, 74. The input optical fiber 22 and a first collector optical fiber 76 extend through the inlet and outlet couplings 72, 74 and into the inlet and discharge ends 66, 68 of the flow cell 70, respectively. Preferably, the input and first collector optical fibers 22, 76 are fixedly mounted to the inlet and outlet couplings 72, 74, respectively. Two optical couplers 78, 80, positioned intermediate the ends 82, 84 of the input optical fiber 22 and the first collector optical fiber 76, couple second and third collector optical fibers 86, 88 to the flow cell 70. The distance between the end 82 of the input optical fiber 22 and the end 84 of the first collector optical fiber 76 and the positions of optical couplers 78 and 80 define long, intermediate and short path lengths, respectively. The length of the path lengths are determined by the required dynamic range of the flow cell assembly. An optical switch 32 with three positions coupled to the collector optical fibers 76, 86, 88 and is used to selectively couple the light from a particular path length to the detector module 16.

Figure 4:
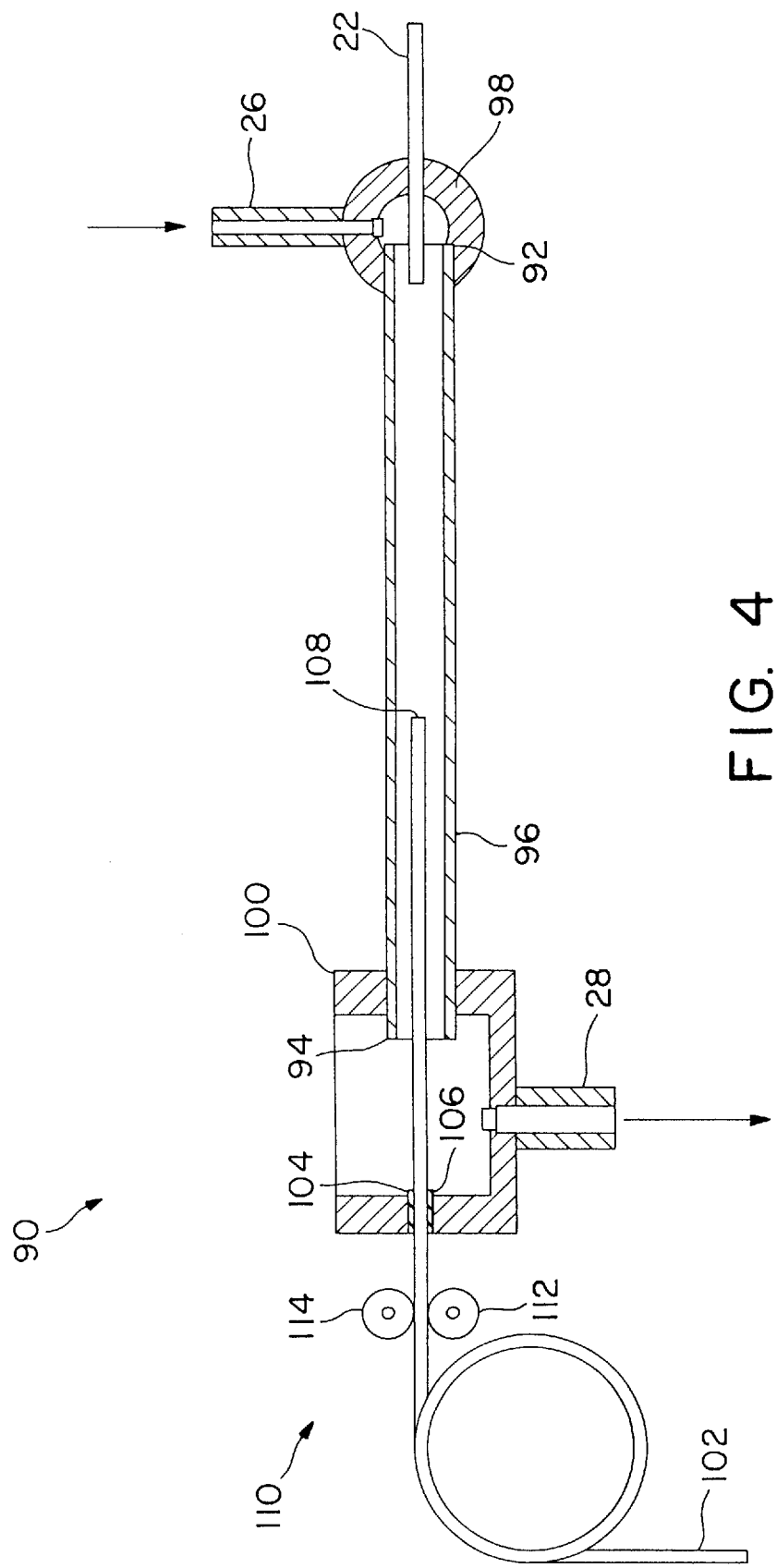
FIG. 4 is a schematic diagram of a third embodiment of the flow cell assembly of FIG. 1.

In the third embodiment of the flow cell assembly 90 (FIG. 4), the inlet and discharge ends 92, 94 of the flow cell 96 are mounted to the inlet and discharge tubes 26, 28 by inlet and outlet couplings 98, 100. The input optical fiber 22 extends through the inlet coupling 98 into the inlet end 92 of the flow cell 96 and is preferably fixedly mounted to the inlet coupling 98. A collector optical fiber 102 extends through an opening 104 in the outlet coupling 100 into the discharge end 94 of the flow cell 96 and is axially moveable within the flow cell 96. A bushing 106, preferably composed of Teflon™, seals opening 104 and provides a low-friction interface between collector optical fiber 102 and outlet coupling 100. The sensitivity of the flow cell 96 can then be adjusted by moving the tip 108 of the collector optical fiber 102 within the waveguide 96 to change its optical path length. A drive mechanism 110 is provided to move the collector optical fiber 102 within the flow cell 96. Such a drive mechanism 110 may include a drive pulley 112 and an idler pulley 114 disposed on opposite sides of the collector optical fiber 102.

Since a conventional optical fiber will be weakened after immersion in water, optical fibers with a hermetically sealed buffer coating have to be used. Hermetically sealed optical fibers buffered with aluminum, copper or gold are currently commercially available. Although the adhesion of the aluminum or copper coating to the fibers is very strong, the aluminum and copper cannot withstand the strong, caustic type of cleaning reagents commonly used for cleaning flow cells. Consequently, such optical fibers require an additional polyimide coating to protect the copper or aluminum coating. Another possibility would be to use a stainless steel Nitinol tubing with a thin wall.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A photometric detection system for analyzing a sample fluid, the system comprising:
    a light source;
    a detector;
    a flow cell assembly including
        a tubular liquid core waveguide having an inlet end adapted for receiving a flow of the sample fluid and a discharge end adapted for discharging the flow of sample fluid, the inlet and discharge ends defining a length;
        first coupling means for optically coupling the light source to the waveguide at a first position along the length of the waveguide;
        second coupling means for optically coupling the detector to the waveguide at a second position along the length of the waveguide, the second coupling means comprising a plurality of collector optical fibers, each of the collector optical fibers having oppositely disposed light receiving and light emitting ends, the light receiving end of each collector optical fiber being coupled to the waveguide at a collection position longitudinally spaced from the collection position of each other collector optical fiber, the first and second positions defining an optical path length; and
        means for varying the second position relative to the first position whereby the optical path length is selectively varied.

2. The photometric detection system of claim 1 wherein the means for varying the second position comprises an optical switch having an outlet port optically coupled to the detector and a plurality of input ports, each of the light emitting ends of the collector optical fibers being optically coupled to an input port of the optical switch, the optical switch selectively coupling a one of the optical path lengths to the detector.

3. The photometric detection system of claim 2 wherein first, second, third and fourth collector optical fibers are coupled to the waveguide at collection positions longitudinally spaced 2 cm, 10 cm, 50 cm and 200 cm, respectively, from the first position.

4. The photometric detection system of claim 3 wherein the length of the waveguide is 200 cm and the collection position for the fourth collector optical fiber is proximate to the discharge end of the waveguide.

5. The photometric detection system of claim 2 wherein first, second and third collector optical fibers are coupled to the waveguide, the collection position for the third collector optical fiber being proximate to the discharge end of the waveguide.

6. A photometric detection system for analyzing a sample fluid, the system comprising:
    a light source;
    a detector;
    a flow cell assembly including
        a tubular liquid core waveguide having an inlet end adapted for receiving a flow of the sample fluid and a discharge end adapted for discharging the flow of sample fluid, the inlet and discharge ends defining a length;
        first coupling means for optically coupling the light source to the waveguide at a first position along the length of the waveguide;
        second coupling means for optically coupling the detector to the waveguide at a second position along the length of the waveguide, the first and second positions defining an optical path length; and
        means for varying the second position relative to the first position whereby the optical path length is selectively varied;
    wherein at least one of the coupling means comprises a plurality of optical fibers, each of the optical fibers having oppositely disposed first and second ends, the first end of each optical fiber being coupled to the waveguide at a coupling position longitudinally spaced from the coupling position of each other optical fiber.

7. The photometric detection system of claim 6 wherein the means for varying the second position comprises at least one optical switch having a first port optically coupled to the light source or the detector and a plurality of second ports, each of the second ends of the optical fibers being optically coupled to a second port of the optical switch.

8. A flow cell assembly for a photometric detection system for analyzing a sample fluid, the photometric detection system including a light source and a detector, the assembly comprising:
    a tubular liquid core waveguide having an inlet end adapted for receiving a flow of the sample fluid and a discharge end adapted for discharging the flow of sample fluid, the inlet and discharge ends defining a length;
    an input optical fiber having oppositely disposed light receiving and light emitting ends, the light receiving end of the input optical fiber being adapted for receiving light from the light source, the light emitting end being optically coupled to the waveguide at an emission position along the length of the waveguide;
    a plurality of collector optical fibers, each of the collector optical fibers having oppositely disposed light receiving and light emitting ends, the light receiving end of each collector optical fiber being optically coupled to the waveguide at a collection position longitudinally spaced from the collection position of each other collector optical fiber, each collection position and the emission position defining an optical path length; and an optical switch having an outlet port and a plurality of input ports, the outlet port being adapted for transmitting light to the detector, each of the light emitting ends of the collector optical fibers being optically coupled to an input port of the optical switch, whereby the optical switch selectively couples a one of the optical path lengths to the detector.

9. The flow cell assembly of claim 8 comprising first, second, third and fourth collector optical fibers coupled to the waveguide at collection positions longitudinally spaced 2 cm, 10 cm, 50 cm and 200 cm, respectively, from the emission position.

\* \* \* \* \*